United States Patent
Hohlbein et al.

(10) Patent No.: US 7,472,448 B2
(45) Date of Patent: Jan. 6, 2009

(54) TOOTHBRUSH WITH ADJUSTABLE HAND GRIP

(75) Inventors: Douglas Hohlbein, Pennington, NJ (US); Natan Vaisman, Larchmont, NY (US)

(73) Assignee: Colgate-Palmolive Company, New York, NY (US)

( * ) Notice: Subject to any disclaimer, the term of this patent is extended or adjusted under 35 U.S.C. 154(b) by 638 days.

(21) Appl. No.: 11/113,932

(22) Filed: Apr. 25, 2005

(65) Prior Publication Data

US 2005/0186014 A1 Aug. 25, 2005

Related U.S. Application Data

(63) Continuation of application No. PCT/US03/33890, filed on Oct. 24, 2003.

(60) Provisional application No. 60/421,514, filed on Oct. 25, 2002.

(51) Int. Cl.
*A46B 5/02* (2006.01)
(52) U.S. Cl. .................... 15/167.1; 15/143.1
(58) Field of Classification Search ........... 15/143.1, 15/167.1
See application file for complete search history.

(56) References Cited

U.S. PATENT DOCUMENTS

| | | | | |
|---|---|---|---|---|
| 4,429,434 A | * | 2/1984 | Sung-shan | 15/341 |
| 4,621,387 A | | 11/1986 | Noser | |
| 4,870,983 A | | 10/1989 | Wang | |
| 5,000,599 A | * | 3/1991 | McCall et al. | 401/6 |
| 5,713,104 A | | 2/1998 | Giampaolo, Jr. | |
| 6,049,936 A | | 4/2000 | Holley | |
| 6,647,582 B1 | * | 11/2003 | Rechelbacher | 15/143.1 |

FOREIGN PATENT DOCUMENTS

| | | |
|---|---|---|
| RU | 2013973 C1 | 6/1994 |
| RU | 2041695 C1 | 8/1995 |
| SU | 1583079 A1 | 8/1990 |

OTHER PUBLICATIONS

Derwent 1995-168434, 1999, "Toothbrush with Additional Inflatable Elastic Handle".

* cited by examiner

*Primary Examiner*—Randall Chin
(74) *Attorney, Agent, or Firm*—Amy M. Fernandez

(57) ABSTRACT

A toothbrush includes a hollow handle which has an outer sleeve made of an elastomeric material which can be expanded or contracted to provide an adjustable diameter grip.

4 Claims, 2 Drawing Sheets

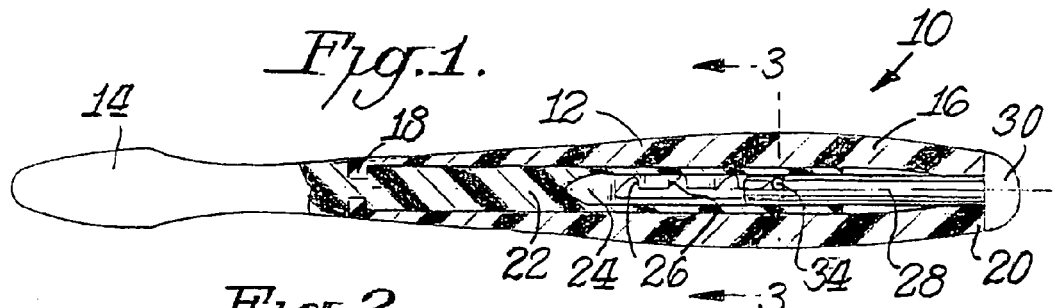
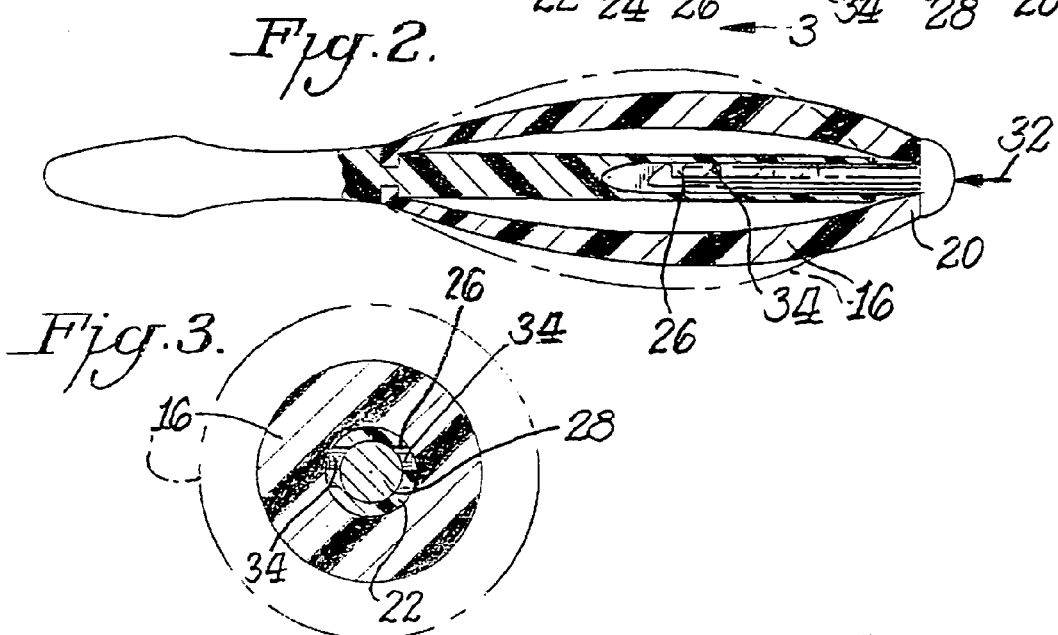
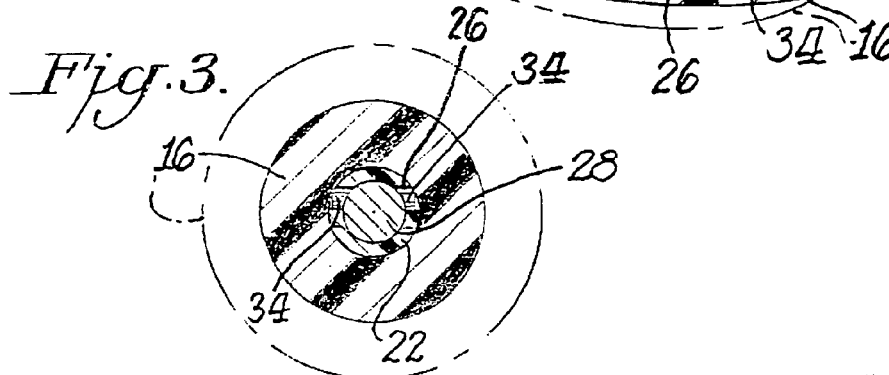
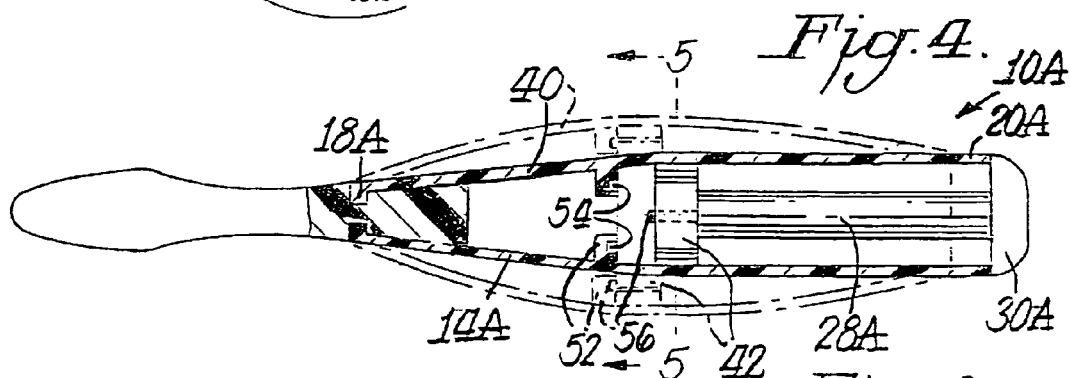
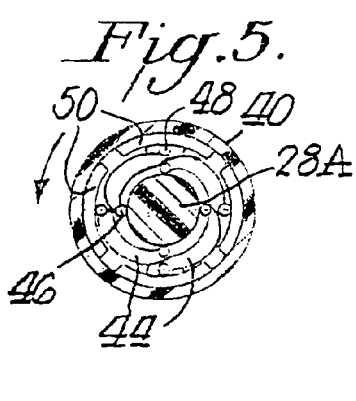
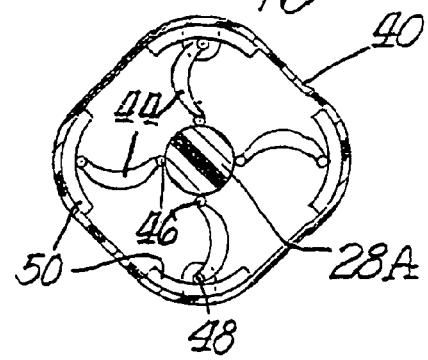

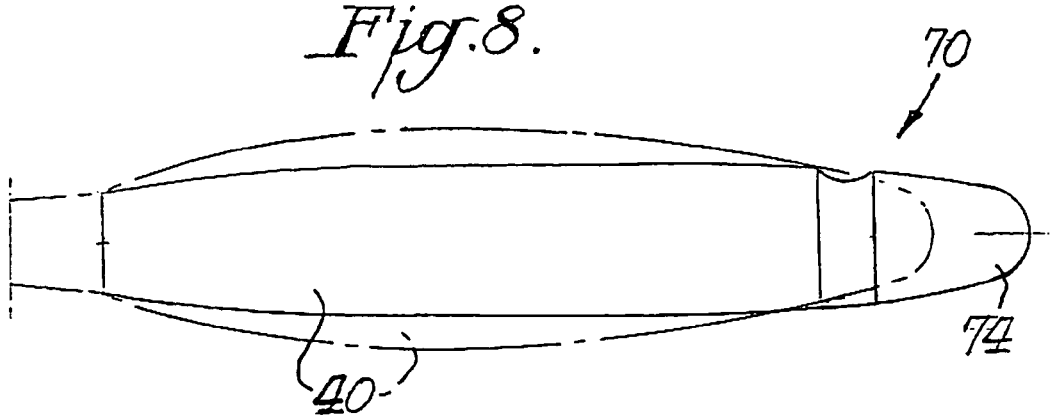
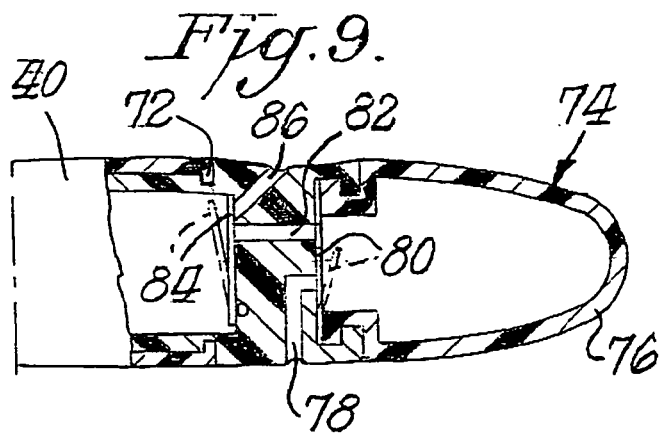
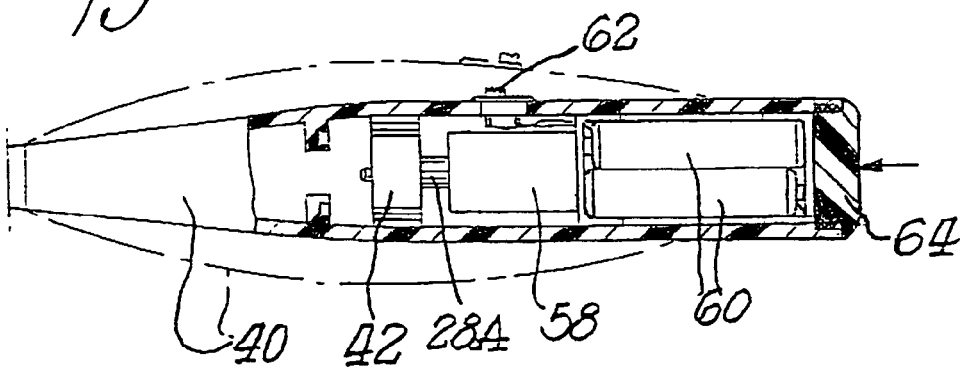

TOOTHBRUSH WITH ADJUSTABLE HAND GRIP

This is a continuation of International Application PCT/US03/33890, filed Oct. 24, 2003, which claims the benefit of U.S. Application 60/421,514, filed Oct. 25, 2002, both of which are incorporated herein by reference in their entirety.

BACKGROUND OF THE INVENTION

It has been found that there is a preference by users of toothbrushes to have a number of different gripping styles which could be used by the consumers when brushing their teeth. Given these different styles it is difficult to design one handle shape which will accommodate this multitude of gripping styles. It would be desirable if it were possible to provide a toothbrush handle having the capability of being adjustable in its diameter and to a lesser extent in its overall length. Such a handle with an adjustable grip would lend itself to help people with different types of disabilities, such as arthritis, to properly brush their teeth.

SUMMARY OF THE INVENTION

An object of this invention is to provide a toothbrush with an adjustable handle grip.

A further object of this invention is to provide such a toothbrush wherein the diameter of the grip could be easily adjusted by a consumer.

In accordance with this invention the toothbrush includes a handle having a head attached at one end of the handle. The head carries cleaning elements, such as bristles. The handle is hollow and includes an outer sleeve made of an elastomeric material. The sleeve includes a first end disposed toward the head and a second end located remote from the head with a central portion between the ends. The central portion is expandable so as to increase its diameter in accordance with the desires of a consumer.

In one practice of the invention, the expansion results from the application of force within the hollow handle outwardly against the central portion so that the central portion expands from a first diameter to a larger second diameter. During the expansion the first end of the sleeve remains anchored at a constant distance from the head in both the first diameter and second diameter conditions of the central portion. In one embodiment of this invention the sleeve is made from a soft thick compressible material which expands when the longitudinal force is applied against the second or outer end of the sleeve to cause the length of the handle to contract while the sleeve bulges outwardly.

In a further embodiment of this invention the sleeve is in the form of a thin elastic skin which is expanded when a knob at the second end of the sleeve is rotated to cause force applicating members which are part of an expansion wheel to move outwardly and press against the inner surface of the sleeve. The force applicating members may be curved spokes which are pivoted to the shaft and pivoted against the sleeve. The spokes are in a generally tight circle before the sleeve is expanded. The spokes are then rotated into a radial direction on their shaft to cause the sleeve to expand.

In a still further embodiment of this invention the sleeve is in the form of a thin elastic skin over the expansion chamber. The skin is stretched outwardly under the pressure of air within the chamber in the central portion of a handle. The air is forced into the chamber by a squeeze pump on the handle.

THE DRAWINGS

FIG. 1 is a top plan view partially broken away and in section of a toothbrush, in accordance with one embodiment of this invention;

FIG. 2 is a view similar to FIG. 1 showing the toothbrush in an expanded condition;

FIG. 3 is a cross-sectional view taken through FIG. 1 along the line 3-3;

FIG. 4 is a top plan view partially broken away and in section of a further toothbrush in accordance with a second embodiment of this invention;

FIG. 5 is a cross-sectional view taken through FIG. 4 along the line 5-5;

FIG. 6 is a view similar to FIG. 5 showing the toothbrush handle in its expanded condition;

FIG. 7 is a side elevational view of a modified form of the toothbrush that is shown in FIGS. 4-6 wherein the expansion is in response to a motor drive;

FIG. 8 is a fragmental side elevational view of yet another toothbrush handle in accordance with a further embodiment of this invention; and FIG. 9 is a fragmental side elevational view of a portion of the toothbrush shown in FIG. 8.

DETAILED DESCRIPTION

The present invention is directed to providing a single toothbrush handle structure which is capable of being adjusted in its diameter. In one practice of the invention the adjustment results from the application of a force in the longitudinal direction to cause the handle to bulge outwardly. In a second practice of the invention the adjustment results from a rotational movement applied to a portion of the handle. In a third embodiment of this invention the expansion or adjustability results from the application of pressure namely from the pumping of air into the hollow handle to cause the handle to bulge outwardly without requiring any longitudinal or rotational movements by the consumer.

FIGS. 1-3 illustrate a toothbrush 10 in accordance with one embodiment of this invention. As shown therein toothbrush 10 includes a handle 12 and a head 14. Head 14 would carry any suitable number of cleaning elements such as tufts of bristles as is known in the art. Any suitable number, type, orientation, etc. of cleaning elements may be used in the various practices of this invention. The invention is particularly directed to providing structure which causes a portion of the handle to bulge outwardly so as to increase its diameter.

As shown in FIGS. 1-2 the handle 12 includes an outer hollow sleeve 16 made of an elastomeric material which is generally soft and thick as well as being compressible. A first end 18 of the sleeve 16 is anchored at a location in the general area of the head 14. The second or remote end 20 of sleeve 16 is located at the opposite end of handle 12. As illustrated a hollow tubular member 22 is mounted within the hollow sleeve 16. Member 22 includes a passageway 24 which is provided with locking structure 26 at spaced locations along its length. An elongated shaft 28 is located axially within the passageway 24 of tubular structure 22. Shaft 28 may terminate in a knob 30 which abuts against the outer surface of second or remote end 20 of sleeve 16. A portion of sleeve 16 between ends 18 and 20 is the central portion which is capable of being expanded from a first minimum diameter illustrated in FIG. 1 to an enlarged second diameter the size of which would vary in accordance with the intent of the consumer. FIG. 2, for example, shows one enlarged diameter illustrated in solid lines and a second larger diameter illustrated in phantom lines.

In order to expand the size or diameter of the central portion of sleeve 16 force is applied in the longitudinal direction as shown by the arrow 32 in FIG. 2. Because end 18 is anchored, the application of the longitudinal force causes the sleeve 16 to bulge outwardly thereby increasing its diameter. As the diameter is increased the overall length of the handle and particularly the sleeve 16 is decreased. This is also shown in FIG. 2.

Any suitable structure may be used for creating the inward movement of remote end 20 of sleeve 16 and then locking the remote end in position to prevent a return movement when the desired diameter has been reached. FIGS. 1-3 illustrate one form of force applicating structure which includes the shaft 28 to have a retaining pin 34. Such a pin 34 could extend on each side of shaft 28 as shown in FIG. 3. In practice shaft 28 would be moved inwardly by pressing against knob 30. Retaining pins 34 are located for movement through passageway 24 by either pressing against the locking structure 26 as the pins are forced past the locking structure. When the desired diameter has been reached the force 32 is no longer applied. Pins 34 are then permitted to enter the locking structure 26 to prevent a rearward or return movement of shaft 28 which would otherwise result in the sleeve 16 returning to its original position.

The locking structure may be of any suitable form. FIGS. 1-2 illustrate the locking structure 26 to be of the bayonet type. If desired the locking structure could be similar to a rack with the teeth inclined in a direction opposite that of structure 26. The pins 34 would act as pinions which would travel over the teeth of the rack and then be held in position when the desired diameter is reached. Other mechanisms could include some slight rotational movement in addition to the longitudinal movement so that the shaft 28 could be rotated sufficiently to engage the pins 34 with the locking structure 26 of tubular member 22 when the desired diameter has been reached. Still other mechanisms such as screw threads could also be used.

If desired the expansion of the soft outer sleeve 16 could be assisted by a set of longitudinal plastic slats or wires which would also provide for a more uniform expansion. Such slats or wires would be mounted at one end to shaft 28 near its knob 30 and mounted at the opposite end near anchor end 18 of sleeve 16. When force 32 is applied to move shaft 28 inwardly the slats or wires would bulge outwardly. Since the slats or wires would be disposed against the inner surface of sleeve 16 the outward bulging of the slats or wires would cause the sleeve 16 to similarly bulge outwardly. The provision of such slats or wires could be in addition to or could be instead of having the tubular member 24 and its locking structure 26.

FIGS. 4-6 illustrate a further embodiment of this invention wherein the toothbrush 10A has its sleeve in the form of a thin expandable skin 40. The skin 40 of hollow handle 14A would have an anchor end 18A and a remote end 20A. Sleeve 40 would be expanded as a result of a rotational movement applied to the handle rather than the longitudinal movement of the handle in FIGS. 1-3.

As shown in FIGS. 4-6 a shaft 28A is provided within the hollow handle 14A. Shaft 28A terminates in an exposed knob 30A which abuts against remote end 20A of skin 40. An expansion wheel 42 is mounted on shaft 28A. Expansion wheel 42 is in the form of a plurality of force transmitting members. As best shown in FIGS. 5-6 these force transmitting members are spokes 44 which are preferably curved. One end 46 of each spoke 44 is pivotally mounted to shaft 28A. The opposite end 48 of each spoke 44 is pivotally mounted to skin 40 such as by being mounted to reinforcing shoe 50 with each shoe 50 being permanently secured to the inner surface of skin 40. In the initial condition shown in solid lines in FIG. 4 and also shown in FIG. 5 the spokes 44 are disposed in a very tight circle in this collapsed condition. Thus, skin 40 is at its minimum diameter. As knob 30A is rotated shaft 28A is also rotated causing the spokes 44 to move toward a radial condition pointing outwards from the longitudinal axis of the handle as shown in FIG. 6. By moving the spokes 44 in a radial direction the skin 40 is caused to expand outwardly to the position shown in FIG. 6 and also shown in phantom in FIG. 4. Where skin 40 is made of a stretchable material, the length of the handle remains the same when the skin has been expanded. Where skin 40 is less stretchable, the handle length decreases as skin 40 expands.

If desired, the inner surface of skin or sleeve 40 may include an inwardly extending partition 52 having detents 54.

Wheel 42 may likewise include one or more pins 56 such as located on the spokes 44 so that as the spokes extend in a more radial direction causing the skin 40 to expand the pins 54, which could also function as the pivot pins for the ends 48 of spokes 44, would remain generally in line with the detents 54.

The knob 30A could be moved inwardly to cause the pins 56 to be locked into detents 54 thereby preventing any reverse rotation of shaft 28A. Alternatively, such added anti-rotational structure could be omitted and the length of handle and its sleeve 40 could remain constant even while the skin or sleeve 40 expands since the skin 40 is made of a stretchable or expandable material which need not be reduced in length in order to permit the expansion as was the case for sleeve 16 of FIGS. 1-3.

FIG. 7 shows a variation of the embodiment of FIGS. 4-6 where the rotation of the shaft is electrically controlled. Thus, as shown in FIG. 7 the shaft 28A is the shaft of a motor 58 powered by batteries 60 under the control of switch 62 so that the actuation of switch 62 turns on the motor 58 to rotate shaft 28A and expansion wheel 42. The handle may be closed by threaded cap 64 which would permit selective access into the interior of the handle for the installation and replacement of batteries 60.

FIGS. 8-9 illustrate yet another embodiment of this invention wherein the toothbrush 70 has a sleeve in the form of an elastic outer skin 40 anchored at one end near the head and anchored at the other end 72 to a pump structure 74. Pump structure 74 includes a squeeze pump 76. Atmospheric air enters the pump 76 through an air intake passage 78 having a one way valve 80. When pump 76 is squeezed the air within the pump 76 flows through passage 82 past one way valve 84 into the hollow interior which is covered by skin 40. The pump also includes a bleed valve 86. As air is pumped into the hollow interior the chamber of the hollow interior must expand to accommodate the incoming air. This expansion results in providing an air pressure against the inner surface of skin 40 to cause the skin 40 to bulge outwardly. In this embodiment of the invention the length of the handle remains the same as its diameter is increased or inflated. Alternatively where skin 40 is less stretchable, the expansion of skin 40 pulls the pump end of the handle inwardly to decrease the length of the handle.

A variation of the toothbrush 70 shown in FIGS. 8-9 would be to provide a bellows formation within the chamber closed by the elastomeric sleeve or skin 40. Air could be pumped into the bellows formation to cause the bellows to expand and thereby expand the skin. The invention could also be practiced where instead of air a liquid or other fluid or gas could be provided in a sac and forced into the bellows formation where the fluid could pressurize and cause the bellows to expand.

In each of the embodiments described herein it is possible to reduce the diameter of the handle after a preselected expansion has been achieved if it is desired to use a smaller diameter handle. With the embodiment of FIGS. 1-3 there would be a disengagement of the locking structure between shaft 28 and inner tubular member 24 to permit the shaft 28 to be moved toward its original position in a direction away from the head 14. In the embodiment of FIGS. 4-6 the diameter of the expanded handle could be reduced by reversing the direction of rotation of shaft 28A so that the spokes 44 again begin to approach a tighter condition which is less radial. In the embodiment of FIGS. 8-9 air could be expelled through the bleed valve 86 to reduce the amount of air within the hollow handle thereby permitting skin 40 to contract until the desired reduced diameter is reached.

While the various figures illustrate the toothbrushes to be of the manual type the invention could also be practiced with an electrical toothbrush having at least one movable section in the head. The motor and batteries for powering the section could be mounted in a central portion of the handle. The motor shaft for moving the one or more sections of the head would extend through the remainder of the handle and into the head. Such electric toothbrush could include one or more sections which are power driven in one or more different types of manners such as by rotational oscillation, continuous rotation in the same direction, linear oscillation in a longitudinal direction and/or linear oscillation in a transverse direction, as well as a rocking back and forth.

Where a power operated toothbrush is used the batteries for powering the motor could be arranged in longitudinal series instead of being side by side to minimize space requirements. Additionally, small disc type batteries such as used in watches, cameras, etc. could be used for powering the motor.

As should be apparent the invention thus provides a toothbrush having a handle of an initial reduced diameter size. The consumer may then increase the diameter of the handle to achieve the desired diameter for that consumer by simple manipulations of the handle. The invention also provides for the possibility of having different size handle adjustment selectability including reducing the handle diameter from an expanded to a less expanded condition.

What is claimed is:

1. A toothbrush comprising a handle, a head connected to said handle, said head having cleaning elements extending outwardly therefrom, said handle being hollow, said handle having an outer sleeve made of an elastomeric material, said sleeve being a thin expandable skin having a first end disposed toward said head and a second end disposed remote from said head, said sleeve having a central portion between said first end and said second end, said central portion being expandable to selectively increase the diameter of said central portion, force applicating structure in said hollow handle for causing said central portion to expand from a first diameter to a selected larger second diameter, wherein said central portion expands in response to rotational movement of said force applicating structure, and said first end being anchored to remain at a constant distance from said head when said central portion is at said first diameter and is at said second diameter, wherein said force applicating structure includes a rotatable shaft longitudinally mounted within said hollow handle and an expansion wheel mounted on said shaft, said expansion wheel capable of transmitting a force for causing said central portion to expand, wherein said expansion wheel includes a plurality of force transmitting members movable from a tight circular condition toward a generally radial condition with respect to said shaft for causing said central portion to expand.

2. The toothbrush of claim 1 wherein said second end is closer to said head when said central portion is at said second diameter than when said central portion is at said first diameter.

3. The toothbrush of claim 1 wherein said force transmitting members are a plurality of spokes, one end of each said spokes being pivotally mounted to said shaft, and the other end of said spokes being pivotally mounted to said skin.

4. The toothbrush of claim 3 wherein said spokes are curved, said toothbrush further comprising a plurality of spaced shoes mounted circumferentially to said skin, and said spokes being pivotally mounted to said shoes.

* * * * *